（12） United States Patent
Hofmann et al.

(10) Patent No.: US 7,608,462 B2
(45) Date of Patent: Oct. 27, 2009

(54) DRYING SPE CARTRIDGES

(75) Inventors: Martin Hofmann, Rheinstetten (DE); Werner Maas, Boxford, MA (US)

(73) Assignee: Bruker Biospin GmbH, Rheinstetten (DE)

( * ) Notice: Subject to any disclaimer, the term of this patent is extended or adjusted under 35 U.S.C. 154(b) by 770 days.

(21) Appl. No.: 11/114,150

(22) Filed: Apr. 26, 2005

(65) Prior Publication Data

US 2005/0252859 A1 Nov. 17, 2005

(30) Foreign Application Priority Data

May 13, 2004 (DE) .................... 10 2004 024 070

(51) Int. Cl.
G01N 33/50 (2006.01)
G01N 21/27 (2006.01)

(52) U.S. Cl. .................. 436/171; 422/68.1; 422/70; 422/104; 436/86; 436/94; 436/172; 436/174; 436/175; 436/177; 436/178

(58) Field of Classification Search .................. 210/656; 436/161, 171–172, 86, 94, 174–175, 177–178; 422/68.1–70, 82.05, 81, 104
See application file for complete search history.

(56) References Cited

U.S. PATENT DOCUMENTS

| 3,583,230 | A | * | 6/1971 | Patterson | .................. 73/864.85 |
|---|---|---|---|---|---|
| 4,003,713 | A | * | 1/1977 | Bowser | ..................... 422/101 |
| 4,186,187 | A | * | 1/1980 | Jahnsen et al. | ................. 422/64 |
| 4,221,568 | A | * | 9/1980 | Boettger | ..................... 436/48 |
| 4,711,764 | A | * | 12/1987 | Good | ..................... 422/65 |
| 4,766,082 | A | * | 8/1988 | Marteau D'Autry | ........ 436/178 |
| 4,810,471 | A | * | 3/1989 | Wachob et al. | ............... 422/103 |
| 5,260,028 | A | * | 11/1993 | Astle | ........................... 422/81 |
| 5,283,036 | A | * | 2/1994 | Hofmann et al. | ............... 422/70 |
| 5,512,168 | A | * | 4/1996 | Fetner et al. | ............. 210/198.2 |
| 5,531,959 | A | | 7/1996 | Johnson | |
| 5,585,068 | A | * | 12/1996 | Panetz et al. | .................. 422/64 |
| 5,585,070 | A | | 12/1996 | Lessard | |
| 5,591,644 | A | | 1/1997 | Karmen | |
| 5,612,002 | A | | 3/1997 | Cody | |
| 6,045,755 | A | * | 4/2000 | Lebl et al. | ..................... 506/33 |
| 6,261,520 | B1 | * | 7/2001 | Kubacki et al. | ................. 422/63 |
| 6,614,228 | B2 | * | 9/2003 | Hofmann et al. | ............ 324/321 |
| 2004/0013572 | A1 | | 1/2004 | Moore | |

FOREIGN PATENT DOCUMENTS

EP 1 202 054 5/2002
WO WO00/54023 9/2000

* cited by examiner

Primary Examiner—Arlen Soderquist
(74) Attorney, Agent, or Firm—Paul Vincent

(57) ABSTRACT

A method for spectrometric investigation of a plurality of samples dissolved in a solvent comprises: (a) guiding a first solvent with a sample through an SPE cartridge for concentrating the sample in the cartridge; (b) positioning the cartridge in a carrier for a plurality of cartridges; (c) repeating steps (a) and (b) for a desired number of samples; (d) drying the concentrated samples through removal of the residual first solvent, in particular, dehydration or evaporation; (e) dissolving each sample in a second solvent, transferring these dissolved samples from the cartridges to a spectrometer and acquiring a spectrum of each sample. All samples are dried together in step (d) subsequent to steps (b) and (c) while the cartridges with samples are positioned in the carrier. The drying process is thereby considerably accelerated in a straightforward technical manner.

17 Claims, 2 Drawing Sheets

DRYING SPE CARTRIDGES

This application claims Paris Convention priority of 10 2004 024 070.1 filed May 13, 2004 the complete disclosure of which is hereby incorporated by reference.

BACKGROUND OF THE INVENTION

The invention concerns a method for spectrometric investigation of a plurality of samples which are dissolved in a solvent, comprising the following steps:
(a) guiding a first solvent with a sample through an SPE cartridge for concentrating the sample in the cartridge;
(b) positioning the cartridge in a carrier for a plurality of cartridges;
(c) repeating steps (a) and (b) for a desired number of samples;
(d) drying the concentrated samples through evaporation or vaporization of the residual first solvent;
(e) dissolving each sample in a second solvent, transferring the dissolved samples from the cartridges to a spectrometer and acquiring a spectrum of each sample.

A method of this type is disclosed in U.S. Pat. No. 6,614,228.

SPE (solid phase extraction) uses small collecting cartridges (SPE cartridges) for collecting and concentrating previously separated mixtures. These have a similar function to a chromatographic separating column on which the sample is retained and eluated from an appropriate composition of solvents.

U.S. Pat. No. 6,614,228 describes a robot device which provides a plurality of SPE cartridges in a carrier. The robot has two clamping devices for inserting each SPE cartridge into the flow path of the first solvent and sealing it to a back pressure of up to 300 bars. The computer-controlled device permits transfer and maintenance of the desired fraction to and in the SPE cartridge through precise switching of interconnected valves. This process can be repeated several times to concentrate the sample.

The cartridge must be completely dried before transfer of the collected substance to a spectrometer. This is achieved by nitrogen flow through the clamped SPE cartridge. The protonized first solvents are evaporated through drying. In a final step, the collected sample is released from the SPE cartridge using second, deuterized organic solvents, and directly inserted into the spectrometer using a flow probe head or into a spectrometer tube.

Drying takes a long time and can only be accomplished for one cartridge at a time. It generally takes about 20 to 35 minutes to completely dry one cartridge. To prevent reaction of the sample at higher temperatures, precaution is required when heating the nitrogen.

U.S. Pat. No. 5,260,028 discloses a fully automatic solid phase extractor (SPE) and a method for operation thereof with which all samples are dried together to facilitate a faster drying of the samples.

U.S. Pat. No. 5,612,002 discloses a partially automatic device for SPE. Vacuum is utilized to simultaneously draw solvent and inert gas through a plurality of SPE cartridges. Moreover, an individual pressure compensation for each SPE unit is described having an over pressure build-up in each reactor tube which can escape via an open capillary. However, as a consequence thereof, only a fraction of the gas is actually used to dry the samples.

US 2004/0013 572 A1 describes a device for fully automatic solid phase extraction with which a plurality of sample vessels are sealed using a plurality of flat, radial seals.

In contrast thereto, it is the underlying purpose of the present invention to propose a method for spectroscopic investigation of a plurality samples with which the drying process is considerably accelerated and rendered more effective using simple technical means.

SUMMARY OF THE INVENTION

This object is achieved in accordance with the invention in a surprisingly simple and effective manner in that, subsequent to steps (b) and (c), all samples are commonly dried in step (d) using a gas flow which streams through the cartridges with the cartridges and samples being positioned in the carrier, thereby highly reducing the time required for drying.

Passage through the cartridges provides rapid gas flow through the samples to further accelerate drying.

The gas flow is divided into partial flows, with each cartridge having its own partial flow which is guided to and/or from the cartridge. The gas flow strength through a cartridge can be individually adjusted in dependence on the type of sample in the cartridge.

The partial flows through each cartridge are sealed from the surroundings. No gas is lost with this type of sealing, which increases the drying efficiency.

Moreover, each partial flow has a flow resistance which is larger than the maximum flow resistance of a cartridge with dissolved sample. This ensures uniform flow of gas and/or solvent through all cartridges even with varying flow resistances of wet, moist or dry samples in the cartridges or missing cartridges at one or more positions. The gas would otherwise flow substantially through the positions with minimum flow resistance and the drying effect at the other positions would be considerably reduced.

In a particularly preferred variant of the inventive method, the samples are preferably dried in step (d) by an inert gas flow which is preferably heated. A heated gas flow can considerably accelerate drying, and reaction of the gas with the sample can be prevented through use of an inert gas, e.g. nitrogen or helium.

In another preferred further development, the number of partial flows equals the number of cartridge positions on the carrier. This ensures that drying is effected simultaneously even if the carrier is filled with the maximum number of cartridges.

In a preferred further development, the gas flow is guided with overpressure to the cartridges and/or suctioned with underpressure from the cartridges. Drying is accelerated through introduction of gas into the cartridge with overpressure and/or suctioning of the gas from the cartridge with underpressure.

In a further advantageous development, the first solvent is guided from the cartridges to a disposal means in step (d). This ensures environment-friendly disposal of the solvent.

In a preferred method variant, the samples are chromatographically separated prior to step (a). In this previous step, substance components are isolated from a mixture, which is usually present in liquid form, using chromatographic separation, wherein the substance components serve as samples for the subsequent steps.

In a further preferred method variant, the cartridges are cleaned with a third solvent in a cleaning step prior to step (a). In the cleaning step, the cartridges can be conditioned and cleaned with organic solvent, e.g. acetonitrile, and subsequently be equilibrated with water for collecting the sample.

In one particularly advantageous further development, the cleaning step is performed analogously to step (d), wherein drying by the gas flow from step (d) is replaced by a cleaning flow through the cartridge using a third solvent. Both steps can be performed using an identical device during the cleaning step, analog to the drying step.

In an advantageous method variant, the spectrum is acquired in step (e) using magnetic resonance, in particular, NMR. The method increases the sensitivity of acquisition of the spectrum through magnetic resonance methods.

In a further development of this variant, each second solvent is deuterized. During acquisition of an NMR spectrum of a sample with deuterized solvent, the solvent does not influence the measurement.

A drying means for performing step (d) of the method comprises a drying chamber for receiving the carrier with the cartridges in a main chamber, wherein the drying chamber has an inlet for gas and/or a third solvent, a pre-chamber, a wall between pre-chamber and main chamber having passage openings with predetermined flow resistances, means for gas-tight connection of the passage openings to the cartridges and an outlet for gas and/or solvent flows. This drying means permits simultaneous drying of a plurality of samples with simple technical means.

In a special variation, the flow resistances are equal.

In a further embodiment of the drying means, the inlet and outlet are interchanged and the flow direction of gas and/or solvent is reversed compared to the above-mentioned example. This means i.a. that the passage openings in the flow direction may be disposed before or after the carrier comprising the cartridges (or on both sides). The drying means may also be designed to permit drying of the cartridges in both a first flow direction as well as in a second flow direction opposite thereto.

In a particularly preferred embodiment, the means for gas-tight connection comprise a preferably elastic sealing plate with holes at the positions of the passage openings. Pressing of the cartridges against the sealing plate leads to simple sealing from the surroundings.

In a further advantageous embodiment, the means for gas-tight connection of each passage opening has an associated cutting ring against which each cartridge can be pressed. The cutting ring leads to a particularly good sealing effect.

In another advantageous embodiment, the carrier may be moved between at least two fixed positions, one of which serves to supply the carrier with cartridges and/or remove the carrier from the main chamber, wherein, in the other position, the cartridges are connected in a gas-tight manner to the associated passage openings to considerably facilitate handling of the carrier.

In one particularly advantageous embodiment, the carrier comprises a well plate format with cartridge positions which correspond to this format, in particular 96. A carrier of the well plate format has standardized dimensions and can therefore also be introduced into other means which e.g. supply the carrier with cartridges, without requiring adaptation.

Further advantages of the invention can be extracted from the description and the drawing. The features mentioned above and below may be used individually or in arbitrary combination. The embodiments shown and described are not to be understood as exhaustive enumeration but have exemplary character for illustrating the invention.

The invention is shown in the drawing and is explained in more detail with reference to embodiments.

DESCRIPTION OF THE PREFERRED EMBODIMENT

Figure 1:
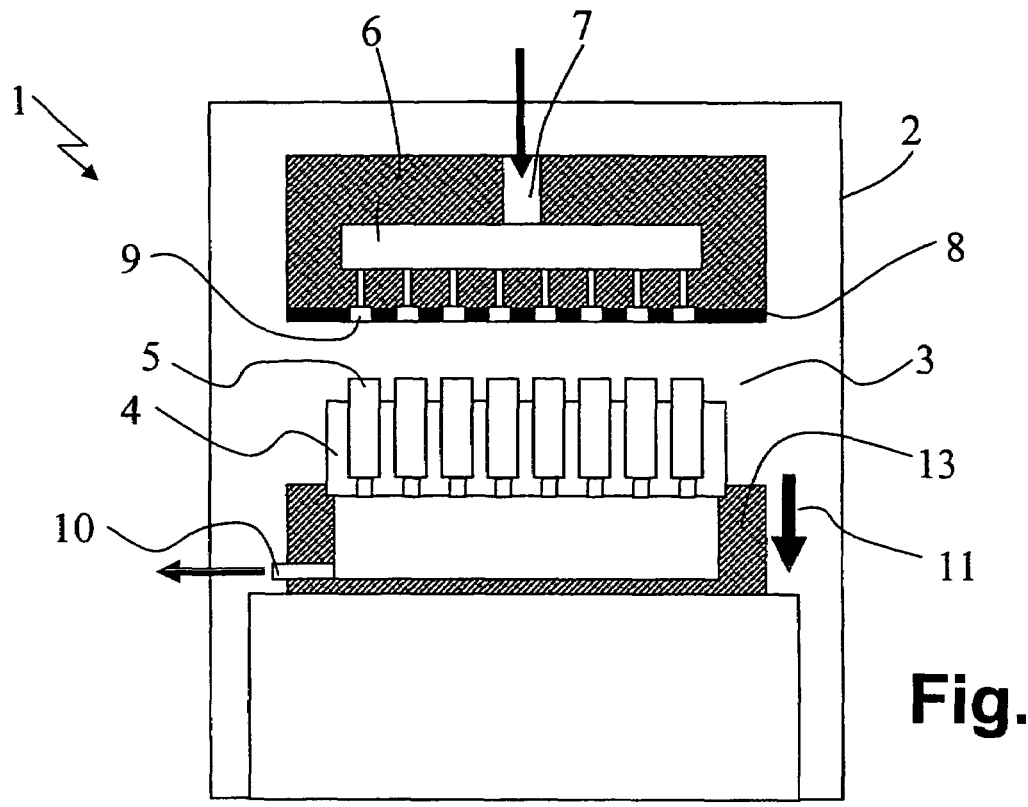
FIG. 1 is a schematic side view of an inventive drying means with a carrier with cartridges in a position for loading and/or removing the carrier.

FIG. 1 schematically shows a side view of the inventive drying means 1 with a drying chamber 2. The drying chamber 2 has a main chamber 3 into which a carrier 4 is introduced with cartridges 5 for solid phase extraction (SPE). The carrier 4 has passage openings on its lower side at the cartridge positions which permit unimpaired gas flow through the cartridges.

The drying chamber 2 also comprises a pre-chamber 6 with an inlet 7 for gas and/or solvent which is connected to the main chamber 3 via an elastic sealing plate 8. The elastic sealing plate 8 has passage openings 9 which correspond to the positions of the cartridges 5 in the carrier 4 to permit gas-tight connection between the cartridges 5 and passage openings 9. An outlet 10 of the drying chamber 2 discharges gas or solvent.

In FIG. 1, the carrier 4 with cartridges 5 is located in a first lower position (shown by the downward arrow 11) for loading and/or removing the carrier 4 or individual cartridges 5 through an opening (not shown) of the drying chamber. The carrier must be moved from the lower position into an upper position in which the cartridges 5 abut the sealing plate 8 to perform common drying or cleaning of all samples.

Figure 2:
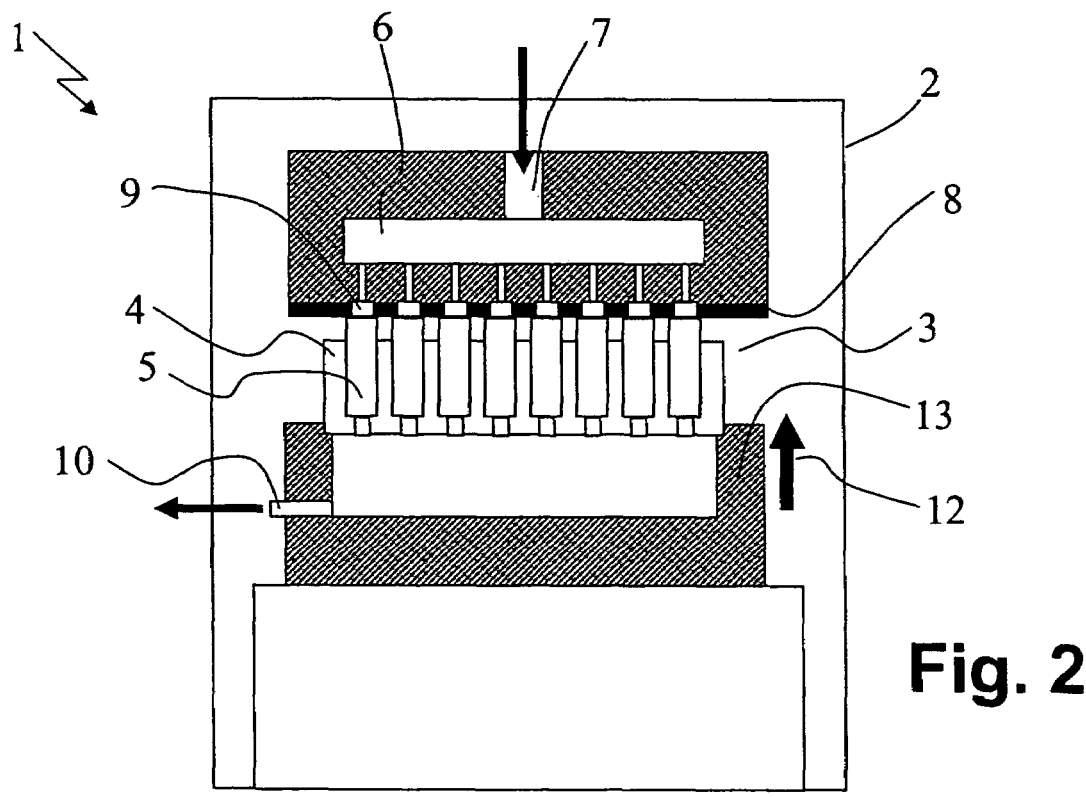
FIG. 2 is a schematic side view of an inventive drying means with a carrier with cartridges in a position for drying the cartridges.

FIG. 2 shows the carrier 4 in the upper position (upward arrow 12) in which the samples are dried or cleaned. The carrier 4 can be moved between the lower position (FIG. 1) and the upper position by a lift 13. In the upper position, the cartridges 5 are pressed against the elastic sealing plate 8 such that the sealing plate is connected to the passage openings 9 in a gas-tight manner.

Figure 3:
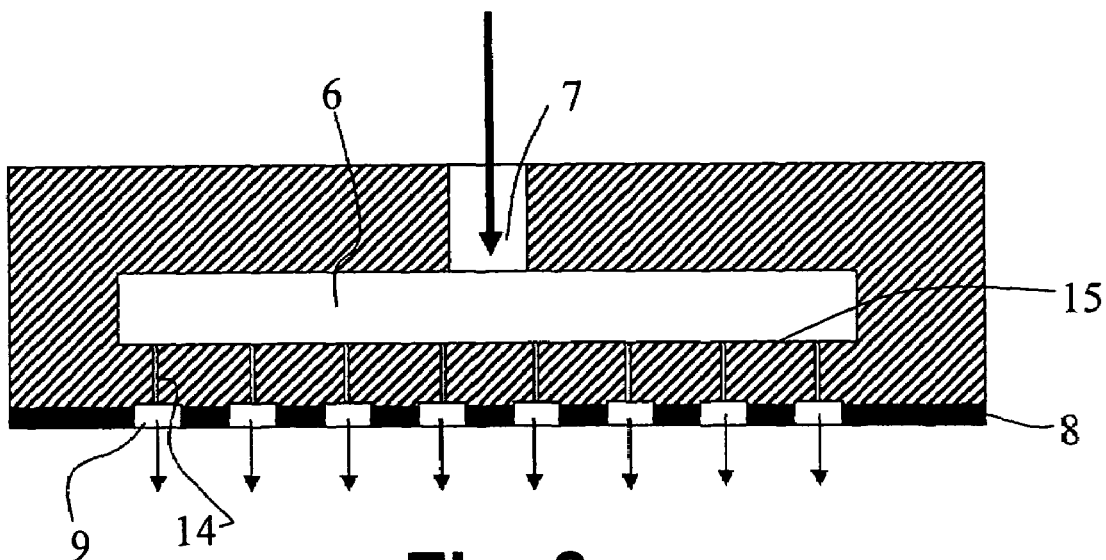
FIG. 3 is a schematic side view of a pre-chamber of the inventive drying means of FIG. 1 and FIG. 2 with a sealing plate with passage openings and restrictions.

When all the samples are dried or cleaned in the upper position, a gas or an organic solvent is introduced under pressure through the inlet 7 into the pre-chamber 6 (shown in detail in FIG. 3). The gas or solvent is divided among a number of restrictions 14 which correspond to the number of cartridge positions which are designed as capillaries and connect a side wall 15 of the pre-chamber 6 to the passage openings 9 of the elastic sealing plate 8. All restrictions 14 have the same flow resistance. The flow resistance of each restriction 14 is larger than the maximum flow resistance of a cartridge 5 with dissolved sample. The gas or solvent passes through the restrictions 14 and through the passage openings 9 (indicated with arrows in FIG. 3). The restrictions 14 permit uniform flow of gas or solvent through the samples even if the flow resistances of the individual samples differ. To accelerate the flow, the outlet 10 is connected to a vacuum pump (not shown) which suctions the gas or solvent from the cartridge 5 through underpressure.

Figure 4:
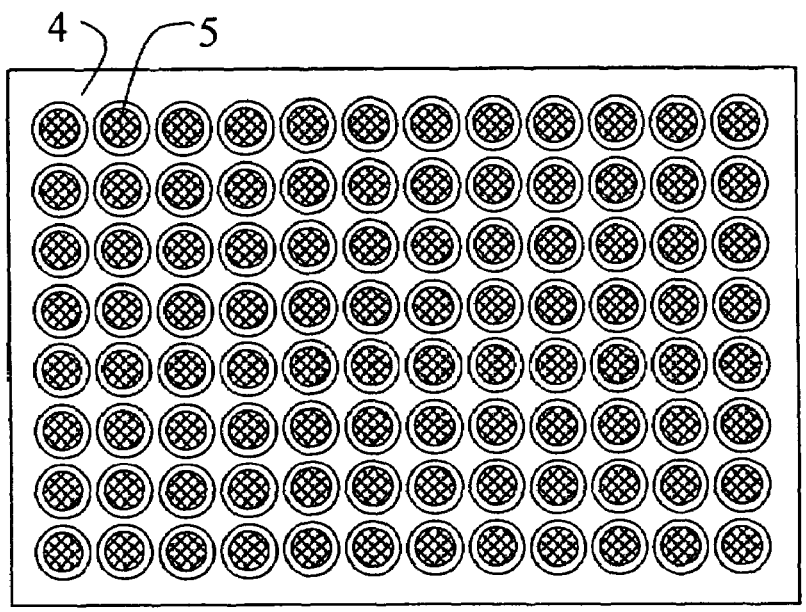
FIG. 4 is a top view of a carrier of the well plate format provided with cartridges.

FIG. 4 shows a top view of the carrier 4 provided with eight by twelve cartridges 5. The dimensions of the carrier correspond to the standardized well plate format. The cartridges 5 can be inserted from above into recesses of the carrier 4.

Figure 5:
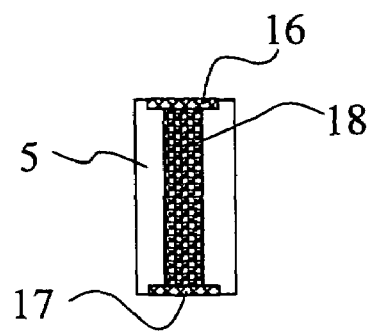
FIG. 5 is a schematic side view of an SPE cartridge.

FIG. 5 shows a side view of a cylindrical cartridge 5 with dimensions of 12 mm by 5 mm. Cover plates 16, 17 are mounted to the two ends of the cartridge 5. A filter material 18 is inserted into a cylindrical cavity between the two cover plates 16, 17. The filter material 18 can retain substances which can be used as samples for acquisition of an NMR spectrum. The cover plates 16, 17 are designed to permit gas or solvent flow therethrough into the filter material 18.

We claim:

1. A method for spectrometric investigation of a plurality of samples dissolved in a solvent, the method comprising the steps of:
   a) guiding a first solvent with a sample through an SPE cartridge for concentrating the sample in the cartridge;
   b) positioning the cartridge in a carrier, the carrier structured to accommodate a plurality of cartridges;
   c) repeating steps a) and b) for a desired number of samples;
   d) drying the samples through evaporation or vaporization of residual first solvent following steps a) through c), wherein all the samples are simultaneously dried together using a gas flow which streams through the cartridges while the cartridges with samples are positioned in the carrier, wherein the gas flow is divided into individual partial flow paths, with each cartridge having its own individual partial flow which is guided to and/or from the cartridge, wherein the partial flow paths through each cartridge are sealed from ambient surroundings, with a flow resistance being provided in each partial flow path that is larger than a maximum flow resistance of any cartridge with dissolved sample;
   e) dissolving each sample in a second solvent;
   f) transferring the dissolved samples from the cartridges to a spectrometer; and
   g) acquiring a spectrum of each sample.

2. The method of claim 1, wherein the samples are dried in step d) by a heated or inert gas flow.

3. The method of claim 1, wherein a number of partial flow paths equals a number of cartridge positions on the carrier.

4. The method of claim 1, wherein the gas flow is guided with overpressure to the cartridges and/or suctioned from the cartridges with underpressure.

5. The method of claim 4, wherein, in step d), the first solvent is supplied from the cartridges to a disposal means.

6. The method of claim 1, wherein each sample is chromatographically separated prior to step a).

7. The method of claim 1, wherein the cartridges are cleaned with a third solvent in a cleaning step prior to step a).

8. The method of claim 7, wherein the cleaning step is performed analogously to step d) with drying by the gas flow of step d) being replaced by a cleaning flow through the cartridges using the third solvent.

9. The method of claim 1, wherein, in step g), the spectrum is acquired using magnetic resonance or NMR.

10. The method of claim 9, wherein each second solvent is deuterized.

11. A drying means for carrying out step d) of claim 1, with a drying chamber for receiving the carrier with the cartridges in a main chamber, wherein the drying chamber has an inlet for gas and/or for a third solvent and a wall between a prechamber and the main chamber, wherein the main chamber has passage openings with predetermined flow resistances, and with means for gas-light connection of the passage openings to the cartridges, as well as an outlet for gas and/or solvent flows.

12. The drying means of claim 11, wherein the flow resistances are equal.

13. The drying means of claim 11, wherein the inlet and outlet are interchanged and flow directions of gas and/or solvent are reversed.

14. The drying means of claim 11, wherein the means for gas-tight connection comprise a preferably elastic sealing plate with openings at positions of the passage openings.

15. The drying means of claim 11, wherein each passage opening has an associated cutting ring as means for gas-tight connection, onto each of which, one cartridge can be pressed.

16. The drying means of claim 11, wherein the carrier can be moved between at least a first and a second fixed position, the first position serving to supply cartridges to the carrier and/or to remove the carrier from the main chamber and, in the second position, the cartridges are connected in a gas-tight manner to the associated passage openings.

17. The drying means of claim 11, wherein the carrier has a well-plate format with cartridge positions corresponding to this format.

* * * * *